(12) United States Patent
Watanabe

(10) Patent No.: US 9,198,564 B2
(45) Date of Patent: Dec. 1, 2015

(54) IMAGE PROCESSING DEVICE AND FLUOROSCOPY DEVICE

(71) Applicant: OLYMPUS CORPORATION, Tokyo (JP)

(72) Inventor: Toshiaki Watanabe, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 316 days.

(21) Appl. No.: 13/654,870

(22) Filed: Oct. 18, 2012

(65) Prior Publication Data

US 2013/0039562 A1    Feb. 14, 2013

Related U.S. Application Data

(63) Continuation of application No. PCT/JP2011/058759, filed on Apr. 7, 2011.

(30) Foreign Application Priority Data

Apr. 28, 2010  (JP) ................. 2010-103544

(51) Int. Cl.
G06K 9/00  (2006.01)
A61B 5/00  (2006.01)
(Continued)

(52) U.S. Cl.
CPC ............. A61B 1/05 (2013.01); A61B 1/00009 (2013.01); A61B 1/043 (2013.01); A61B 1/0638 (2013.01); A61B 5/0071 (2013.01); A61B 5/0084 (2013.01); G06T 7/0012 (2013.01);

(Continued)

(58) Field of Classification Search
None
See application file for complete search history.

(56) References Cited

U.S. PATENT DOCUMENTS 6,111,259 A * 8/2000 Arai ................ 250/459.1
7,932,502 B2 * 4/2011 Kubo et al. ........... 250/458.1
(Continued)

FOREIGN PATENT DOCUMENTS

JP    2007-068896    3/2007
JP       4327380     6/2009
WO  2010/044483 A1  4/2010

OTHER PUBLICATIONS

English Abstract of first publication No. 2002-172082 (JP4327380), dated Jun. 18, 2002.

(Continued)

*Primary Examiner* — Matthew Bella
*Assistant Examiner* — Jose M Torres
(74) *Attorney, Agent, or Firm* — Scully, Scott, Murphy & Presser, P.C.

(57) ABSTRACT

Employed is an image processing device including a fluorescence-image generating unit that images fluorescence generated at a subject irradiated with excitation light and generates a fluorescence image; a white-light-image generating unit that images white light returned from the subject irradiated with illumination light and generates a white-light image; a memory that converts the white-light image to a plurality of color signals constituting a color space; an image computing unit that corrects the plurality of color signals converted by the memory using at least one color signal among the plurality of the color signals and the fluorescence image; an image computing unit that generates a corrected image from the plurality of color signals corrected by the image computing unit; and an image combining unit that combines the fluorescence image generated by the fluorescence-image generating unit and the corrected image generated by the image computing unit.

15 Claims, 9 Drawing Sheets

(51) Int. Cl.
  *A61B 1/05* (2006.01)
  *G06T 7/00* (2006.01)
  *A61B 1/04* (2006.01)
  *A61B 1/00* (2006.01)
  *A61B 1/06* (2006.01)

(52) U.S. Cl.
  CPC .............. *G06T2207/10064* (2013.01); *G06T 2207/10116* (2013.01)

(56) References Cited

U.S. PATENT DOCUMENTS

| | | | |
|---|---|---|---|
| 8,498,695 B2* | 7/2013 | Westwick et al. | 600/478 |
| 2002/0168096 A1* | 11/2002 | Hakamata et al. | 382/132 |
| 2003/0013937 A1* | 1/2003 | Tsujita et al. | 600/109 |
| 2005/0143627 A1* | 6/2005 | Cline et al. | 600/181 |
| 2005/0261592 A1* | 11/2005 | Suga | 600/478 |
| 2007/0046778 A1* | 3/2007 | Ishihara et al. | 348/68 |
| 2009/0122135 A1* | 5/2009 | Matsui | 348/65 |
| 2009/0268010 A1 | 10/2009 | Zhao et al. | |
| 2010/0265321 A1 | 10/2010 | Minai et al. | |
| 2010/0322492 A1* | 12/2010 | Stepp et al. | 382/128 |

OTHER PUBLICATIONS

International Search Report dated Jul. 19, 2011 issued in PCT/JP2011/058759.

Extended Supplementary European Search Report dated May 6, 2014 from related European Application No. 11 77 4776.6.

* cited by examiner

IMAGE PROCESSING DEVICE AND FLUOROSCOPY DEVICE

CROSS REFERENCE TO RELATED APPLICATIONS

This is a continuation of International Application PCT/JP/2011/058759, with an international filing date of Apr. 7, 2011, which is hereby incorporated by reference herein in its entirety. This application claims the benefit of Japanese Patent Application No. 2010-103544, the content of which is incorporated herein by reference.

TECHNICAL FIELD

The present invention relates to an image processing device and a fluoroscopy device.

BACKGROUND ART

In fluoroscopy devices for diagnosing an affected region using a fluorescence agent, there is a known method of assigning color information and luminance information respectively to feature information and shape information of tissue and combining an image showing the tissue feature information and an image showing the tissue shape information (for example, refer to Patent Literature 1).

CITATION LIST

Patent Literature

{PTL 1} Publication of Japanese Patent No. 4327380

SUMMARY OF INVENTION

The present invention employs the following solutions.

A first aspect of the present invention provides an image processing device including a fluorescence-image generating unit configured to image fluorescence generated at a subject irradiated with excitation light and generate a fluorescence image; a return-light-image generating unit configured to image return light returned from the subject irradiated with illumination light and generates a return-light image; a color converting unit configured to convert the return-light image generated by the return-light-image generating unit to a plurality of color signals constituting a color space; a color-signal correcting unit configured to correct the plurality of color signals converted by the color converting unit using at least one of the color signals among the plurality of color signals and the fluorescence image generated by the fluorescence-image generating unit; a corrected-image generating unit configured to generate a corrected image from the plurality of color signals corrected by the color-signal correcting unit; and an image combining unit configured to combine the fluorescence image generated by the fluorescence-image generating unit and the corrected image generated by the corrected-image generating unit.

DESCRIPTION OF EMBODIMENTS

A fluoroscopy device 1 according to an embodiment of the present invention will be described below with reference to the drawings. Here, an example in which the fluoroscopy device 1 according to this embodiment is applied to an endoscope apparatus will be described.

Figure 1:
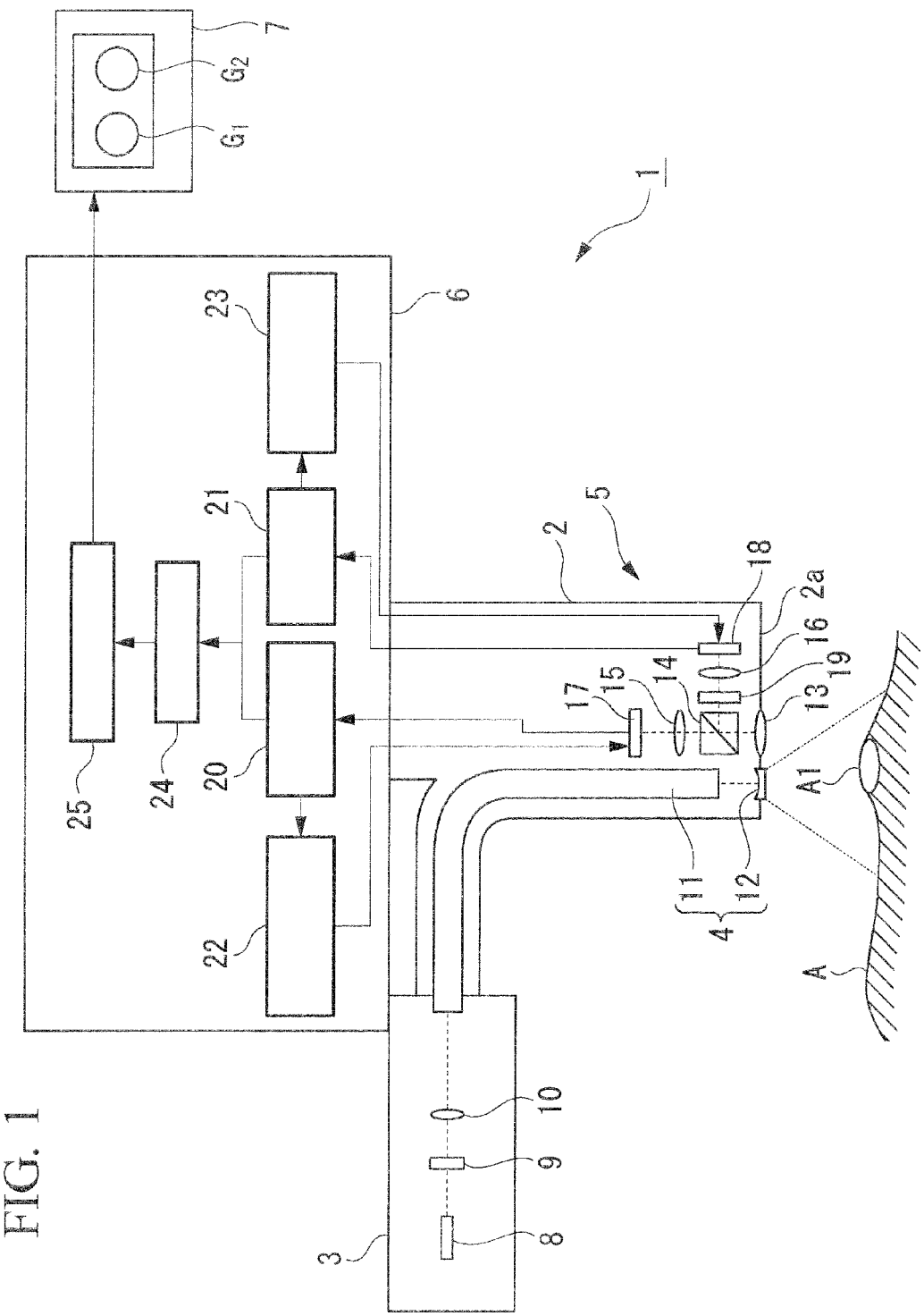
FIG. 1 is a diagram showing, in outline, the configuration of a fluoroscopy device according to an embodiment of the present invention.

As illustrated in FIG. 1, the fluoroscopy device 1 according to this embodiment includes a long, thin insertion part 2 that is to be inserted into the body, a light source (light source unit) 3 that emits illumination light and excitation light, an illumination unit 4 that radiates the illumination light and the excitation light from the light source 3 through the tip of the insertion part 2 toward a subject A, an image acquisition unit 5 that is installed in the tip of the insertion part 2 and acquires image information about the subject A, an image processing device 6 that is positioned on the base side of the insertion part 2 and processes the image information acquired by the image acquisition unit 5, and a monitor (image display unit) 7 that displays images processed by the image processing device 6.

The light source 3 includes a xenon lamp 8, a filter 9 that segregates excitation light and white light (illumination light) within a wavelength band of, for example, 400 to 750 nm in the illumination light generated at the xenon lamp 8, and a coupling lens 10 that focuses the excitation light and white light segregated by the filter 9.

The illumination unit 4 includes a light guide fiber 11 that extends along substantially the entire length of the insertion part 2 in the longitudinal direction and guides the excitation light and white light focused by the coupling lens 10 and an illumination optical system 12 that is provided at the tip of the insertion part 2 and spreads out and radiates the excitation light and white light guided through the light guide fiber 11 onto the subject A opposing the tip surface 2a of the insertion part 2.

The image acquisition unit 5 includes an objective lens 13 that collects return light returning from a predetermined observation area of the subject A, a dichroic mirror 14 that reflects light having a wavelength equal to or longer than the excitation wavelength (excitation light and fluorescence) and transmits white light having a wavelength shorter than the excitation wavelength, among the return light collected by the objective lens 13, two focusing lenses 15 and 16 that respectively focus the white light transmitted through the dichroic mirror 14 and the fluorescence reflected at the dichroic mirror 14, a white-light color CCD 17 that acquires an image of the white light focused by the focusing lens 15, and a fluorescence monochrome CCD 18 that acquires an image of the fluorescence focused by the focusing lens 16. In FIG. 1, reference sign 19 represents an excitation-light cut filter that blocks excitation light in the light reflected at the dichroic mirror 14 (for example, only transmits light within the wavelength band of 765 to 850 nm).

The image processing device 6 included, as the functions thereof, the functions of a white-light-image generating unit (return-light image generating unit) 20 that generates a white-light image, a fluorescence-image generating unit 21 that generates a fluorescence image, an automatic exposure-time adjusting unit 22 that adjusts the exposure time of the white-light color CCD 17, an automatic exposure-time adjusting unit 23 that adjusts the exposure time of the fluorescence monochrome CCD 18, a memory (color conversion unit) 24 that stores the color signals for the R, C, and B components of the white-light image, and an image computing unit (color-signal correcting unit, corrected-image generating unit, image combining unit) 25 that corrects the color signals of the R, C, and B components.

The white-light-image generating unit 20 generates a white-light image from the white-light-image data detected by the white-light color CCD 17. The white-light-image generating unit 20 transmits the generated white-light image to the memory 24 and the automatic exposure-time adjusting unit 22.

The fluorescence-image generating unit 21 generates a fluorescence image from the fluorescence-image data detected by the fluorescence monochrome CCD 18. The fluorescence-image generating unit 21 transmits the generated fluorescence image to the memory 24 and the automatic exposure-time adjusting unit 23.

The automatic exposure-time adjusting unit 22 adjusts the exposure time of the white-light color CCD 17 on the basis of the luminance value of the white-light image generated by the white-light-image generating unit 20.

The automatic exposure-time adjusting unit 23 adjusts the exposure time of the fluorescence monochrome CCD 18 on the basis of the luminance value of the fluorescence image generated by the fluorescence-image generating unit 21.

By doing so, the exposure time of the next frame is automatically calculated from each of the generated images to control the exposure time of the respective CCDs.

Note that, although this embodiment describes that the exposure times of the white-light color CCD 17 and the fluorescence monochrome CCD 18 are adjusted by the automatic exposure-time adjusting unit 22 and the automatic exposure-time adjusting unit 23 on the basis of the luminance values of the white-light image and the fluorescence image, the amounts of white light and excitation light emitted from the light source 3 may be controlled, or the gains of the white-light color CCD 17 and the fluorescence monochrome CCD 18 may be adjusted.

Figure 2:
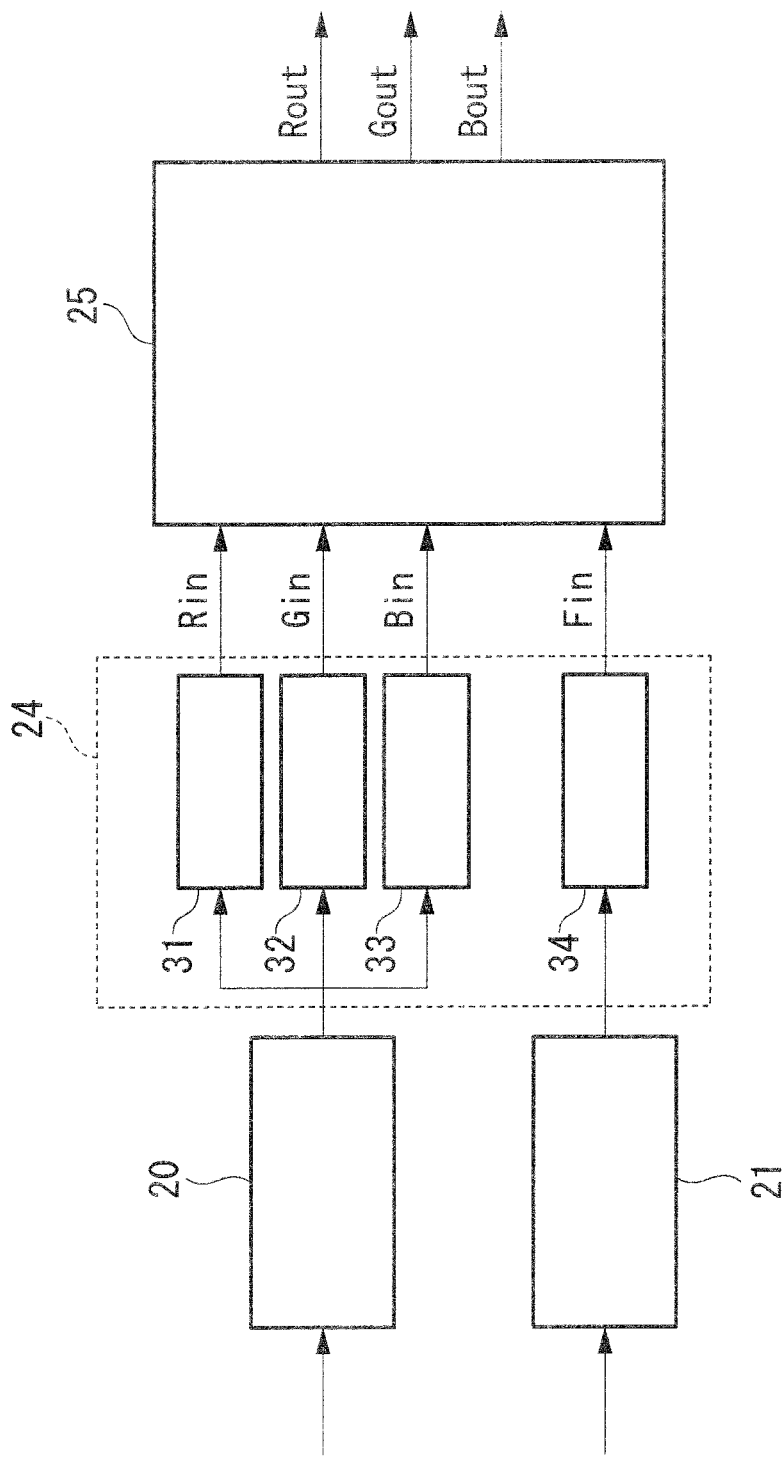
FIG. 2 is a functional block diagram of an image processing device in FIG. 1.

As illustrated in FIG. 2, the memory 24 has an R memory 31, a G memory 32, and a B memory 33 for respectively storing color signals of R, G, and B components of the white-light image and an F memory 34 for storing a fluorescence-image signal.

The memory 24 converts the white-light image generated by the white-light-image generating unit 20 to color signals of R, G, and B components constituting a color space, stores the color signals in the respective memories, and, at the same time, stores the fluorescence-image signal generated by the fluorescence-image generating unit 21 in the F memory 34, and outputs the stored color signals and fluorescence-image signal to the image computing unit 25.

The image computing unit 25 corrects color signals of the white-light image by multiplying each color signal of the white-light image by results of dividing the fluorescence-image signal generated by the fluorescence-image generating unit 21 by at least one of the color signals among the individual color components of the white-light image.

Specifically, the image computing unit 25 corrects the R, G, and B components of the white-light image on the basis of, for example, the following expressions:

$$B_{OUT} = B_{IN} \times (F_{IN}/R_{IN}) \times \alpha,$$

$$G_{OUT} = G_{IN}, \text{ and}$$

$$R_{OUT} = R_{IN} \times (F_{IN}/R_{IN}) \times \alpha,$$

where $B_{OUT}$ is the signal strength of the B component of the corrected image, $G_{OUT}$ is the signal strength of the G component of the corrected image, $R_{OUT}$ is the signal strength of the R component of the corrected image, $B_{IN}$ is the signal strength of the B component of the white-light image, $G_{IN}$ is the signal strength of the G component of the white-light image, $R_{IN}$ is the signal strength of the R component of the white-light image, $F_{IN}$ is the signal strength of the fluorescence image, and $\alpha$ is a coefficient that equals $R_{IN}/F_{IN}$ at a normal site.

Here, the coefficient $\alpha$ is a value preset using a calibration member on the basis of the fluorescence intensity at a normal site in the subject A and, as mentioned above, is a coefficient that equals $R_{IN}/F_{IN}$ at a normal site of the subject A. That is, the coefficient $\alpha$ is a coefficient that satisfies $(F_{IN}/R_{IN}) \times \alpha = 1$ at the normal site of the subject A. Hence, the corrected color signals of the normal site of the subject A are computed as follows:

$$B_{OUT} = B_{IN},$$

$$G_{OUT} = G_{IN}, \text{ and}$$

$$R_{OUT} = R_{IN}.$$

In addition, the image computing unit 25 generates a corrected image from the color signals corrected in this way, combines the generated corrected image and the fluorescence image generated by the fluorescence-image generating unit 21, and outputs the combined image to the monitor 7.

The monitor 7 displays an image in which a white-light image G1 generated by the white-light-image generating unit 20 and a combined image G2 obtained by the image computing unit 25 combining the corrected image and the fluorescence image are positioned side-by-side.

The operation of the fluoroscopy device 1 having the above-described configuration will be described below.

To observe a subject A in a body cavity of a biological subject using the fluoroscopy device 1 according to this embodiment, first, a fluorescence agent that preferentially accumulates at an affected site A1, such as cancer cells or the like, is attached to or caused to be absorbed by the subject A. In such a state, the fluorescence agent is excited to generate fluorescence by irradiating the subject A with excitation light.

Next, the insertion part 2 is inserted into the body cavity such that the tip 2a opposes the subject A. By activating the light source 3 in this state, white light that contains excitation light generated at the xenon lamp 8 and separated by the filter 9 is focused by the coupling lens 10 and is guided to the tip 2a of the insertion part 2 through the light guide fiber 11. Then, the white light is spread out by the illumination optical system 12 and is radiated onto the subject A.

Fluorescence is generated by the fluorescent substance contained in the subject A being excited by excitation light, and part of the white light and excitation light is reflected at the surface of the subject A. The objective lens 13 collects the fluorescence, the white light, and the excitation light, and the dichroic mirror 14 reflects light having a wavelength equal to or longer than the excitation wavelength, i.e., excitation light and fluorescence, while transmitting white light having a wavelength shorter than the excitation wavelength.

The excitation-light cut filter 19 removes the excitation light from the excitation light and the fluorescence reflected at the dichroic mirror 14, so that only the fluorescence is focused by the focusing lens 16 and is imaged by the fluorescence monochrome CCD 18. Accordingly, the fluorescence monochrome CCD 18 acquires fluorescence-image information of the subject A. In addition, the white light transmitted through the dichroic mirror 14 is focused by the focusing lens 15 and is imaged by the white-light color CCD 17. Accordingly, the white-light color CCD 17 acquires white-light-image information of the subject A. Note that, either the fluorescence-image information or the white-light-image information may be acquired first, or they may be acquired simultaneously.

The fluorescence-image information acquired by the fluorescence monochrome CCD 18 and the white-light-image information acquired by the white-light color CCD 17 are respectively sent to the fluorescence-image generating unit 21 and the white-light-image generating unit 20 of the image processing device 6.

The fluorescence-image generating unit 21 generates a two-dimensional fluorescence image based on the fluorescence-image information sent from the fluorescence monochrome CCD 18, and the white-light-image generating unit 20 generates a two-dimensional white-light image based on the white-light-image information sent from the white-light color CCD 17.

At this time, the automatic exposure-time adjusting unit 22 adjusts the exposure time of the white-light color CCD 17, and the automatic exposure-time adjusting unit 23 adjusts the exposure time of the fluorescence monochrome CCD 18.

Next, the white-light image generated by the white-light-image generating unit 20 is converted to color signals of R, G, and B components and is stored in the respective memories in the memory 24; the fluorescence-image signal generated by the fluorescence-image generating unit 21 is also stored in the F memory 34; and the individually stored color signals and fluorescence-image signal are output to the image computing unit 25.

As described above, the image computing unit 25-corrects the color signals of the R, G, and B components of the white-light image based on, for example, the following expressions:

$$B_{OUT} = B_{IN} \times (F_{IN}/R_{IN}) \times \alpha,$$

$$G_{OUT} = G_{IN}, \text{ and}$$

$$R_{OUT} = R_{IN} \times (F_{IN}/R_{IN}) \times \alpha,$$

The image computing unit 25 generates a corrected image from the color signals corrected in such a manner and combines the corrected image and the fluorescence image generated by the fluorescence-image generating unit 21. The combined image combined in this way and the white-light image generated by the white-light-image generating unit 20 are displayed on the monitor 7.

An object of the present invention, which has been conceived in light of the above-described circumstances, is to provide an image processing device and a fluoroscopy device while making it easy to identify an affected site and suppress a change in the color of a normal site.

As described above, with the fluoroscopy device 1 according to this embodiment, the image computing unit 25 uses the color signals of the white-light image and the fluorescence-image signal to correct the color signals of the R, G, and B components of the white light image, to generate a corrected image, and to combine the fluorescence image and the corrected image.

By doing so, the combined image in which, for example, the affected site A1 in biological tissue is distinctively displayed and the normal sites are also corrected so as to appear with equivalent colors to the original can be displayed on the monitor 7. Accordingly, the normal sites can be observed in colors similar to the original colors, while identifying the position and shape of the affected site A1, which makes it possible to improve the observation precision of the subject A.

The affected site A1 can be displayed clearly as a result of the image computing unit 25 correcting the color signals of the R, G, and B components of the white-light image on the basis of the following expressions:

$$B_{OUT} = B_{IN} \times (F_{IN}/R_{IN}) \times \alpha,$$

$$G_{OUT} = G_{IN}, \text{ and}$$

$$R_{OUT} = R_{IN} \times (F_{IN}/R_{IN}) \times \alpha.$$

By correcting the RGB components of the white-light image on the basis of the expressions described above, because the B and R components are increased when the signal strength of the fluorescence image is increased, the affected site appears in a color closer to magenta (purplish red). Here, the G and B components are easily absorbed because the inside of a biological subject is red due to blood, etc. Therefore, by correcting the signal strength of the B and R components using the signal of the R component, which is not easily absorbed inside the biological subject, the color of the normal sites can be corrected. That is, through the above-described procedures, it is possible to display the affected site A1 in magenta (purplish red) in the combined image, as well as to display the normal sites therein in the original color.

First Modification

As a first modification of this embodiment, the coefficient α to be used in the computation by the image computing unit 25 may be automatically set.

Figure 3:
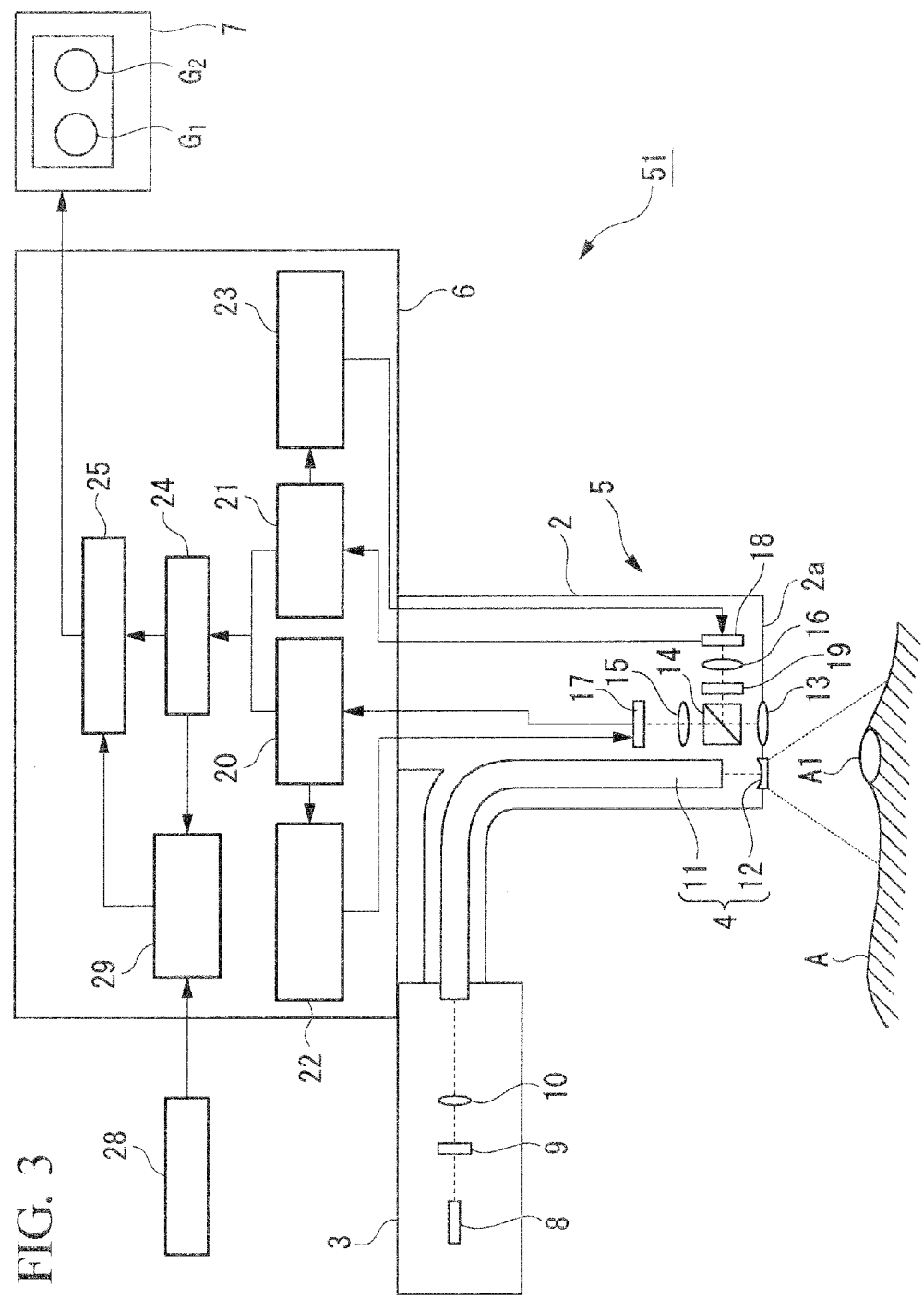
FIG. 3 is a schematic configuration diagram of a fluoroscopy device according to a first modification of the present invention.

As illustrated in FIG. 3, a fluoroscopy device 51 according to this modification includes, in addition to the components illustrated in FIG. 1, an input unit 28, for example, buttons of the like, provided in the operating unit of the insertion part 2 and a parameter setting unit 29 that sets a parameter (coefficient α) based on an instruction input to the input unit 28.

Figure 4:
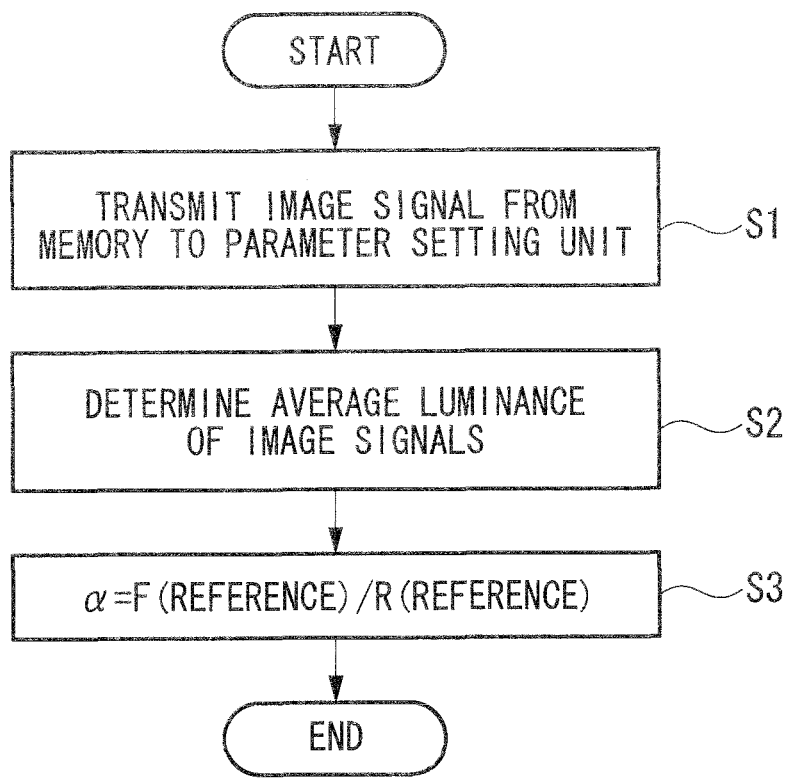
FIG. 4 is a flow chart for explaining the process carried out by the fluoroscopy device in FIG. 3.

The method of determining the coefficient α of the fluoroscopy device 51 according to this modification will be described using the flow chart shown in FIG. 4.

By operating the input unit 28, the color signal used as a reference signal among the color signals of R, G, and B components of the white-light image stored in the memory 24 (the R component in this modification) and the fluorescence-image signal are sent to the parameter setting unit 29 (Step S1).

Figure 5:
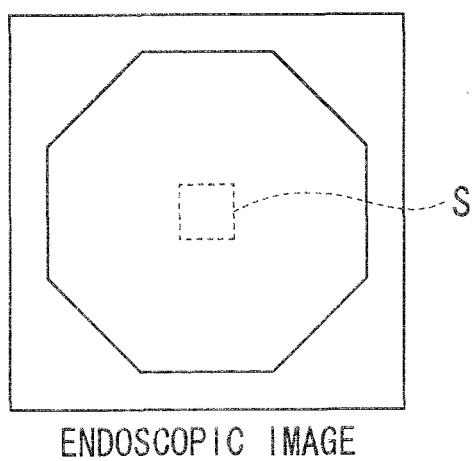
FIG. 5 is an example screen for explaining the process of determining a coefficient in the fluoroscopy device in FIG. 3.

Next, the average luminance of the R component signal of the white-light image and the fluorescence-image signal in a region set in advance is calculated at the parameter setting unit 29 (Step S2). Here, as illustrated in FIG. 5, the region set in advance is, for example, a region S at the center portion of the image.

Next, the coefficient α is calculated by dividing the signal strength of the fluorescence image, which serves as a reference, by the signal strength of the R component (Step S3).

As described above, with the fluoroscopy device 51 according to this modification, the coefficient α for correcting the color signals of the white-light image can be calculated from the fluorescence image acquired by the fluorescence monochrome CCD 18 and the white-light image acquired by the white-light color CCD 17.

Note that, the coefficient α may be calculated from the ratio of the reference gradation values between the fluorescence monochrome CCD 18 and the white-light color COD 17.

Second Modification

As a second modification of this embodiment, the image computing unit 25 may multiply results of dividing at least one signal of the R, G, and B components of the white-light image by the fluorescence image generated by the fluorescence-image generating unit 21 with the signals of the R, G, and B components of the white-light image.

Specifically, the image computing unit 25 corrects the color signals of the R, G, and B components of the white-light image on the basis of, for example, the following expressions:

$$B_{OUT}=B_{IN}\times(R_{IN}/F_{IN})/\alpha,$$

$$G_{OUT}=G_{IN}, \text{ and}$$

$$R_{OUT}=R_{IN}\times(R_{IN}/F_{IN})/\alpha.$$

where $B_{OUT}$ is the signal strength of the B component of the corrected image, $G_{OUT}$ is the signal strength of the G component of the corrected image, $R_{OUT}$ is the signal strength of the R component of the corrected image, $B_{IN}$ is the signal strength of the B component of the white-light image, $G_{IN}$ is the signal strength of the G component of the white-light image, $R_{IN}$ is the signal strength of the R component of the white-light image, $F_{IN}$ is the signal strength of the fluorescence image, and α is a coefficient that equals $R_{IN}/F_{IN}$ at a normal site.

By correcting the RGB components of the white-light image in this way, the B and R components of the corrected image can be decreased when the signal strength of the fluorescence image is increased. That is, through the above-described procedures, it is possible to display only the affected site A1 in green in the combined image, as well as to display the normal sites in the original colors.

Third Modification

As a third modification of this embodiment, the image computing unit 25 may correct the color signals of the R, G, and B components of the white-light image on the basis of, for example, the following expressions:

$$B_{OUT}=B_{IN}\times[\{(F_{IN}/R_{IN})-\alpha\}\times\beta+1],$$

$$G_{OUT}=G_{IN}, \text{ and}$$

$$R_{OUT}=R_{IN}\times[\{(F_{IN}/R_{IN})-\alpha\}\times\beta+1],$$

where $B_{OUT}$ is the signal strength of the B component of the white light corrected image, $G_{OUT}$ is the signal strength of the G component of the corrected image, $R_{OUT}$ is the signal strength of the R component of the corrected image, $B_{IN}$ is the signal strength of the B component of the white-light image, $G_{IN}$ is the signal strength of the G component of the white-light image, $R_{IN}$ is the signal strength of the R component of the white-light image, $F_{IN}$ is the signal strength of the fluorescence image, α is a coefficient that equals $F_{IN}/R_{IN}$ at a normal site, and β is color gain (coefficient set in advance).

By correcting the RGB components of the white-light image in this way, because the B and R components are increased when the signal strength of the fluorescence image is increased, the affected site A1 appears in a color closer to magenta (purplish red). In addition, by including multiplication by the color gain, the color change in the affected site A1 can be increased. Accordingly, it is possible to display the affected site A1 in magenta (purplish red) in the combined image, as well as to display the normal sites therein in the original color.

Fourth Modification

As a fourth modification of this embodiment, the image computing unit 25 may correct the color signals of the R, G, and B components of the white-light image on the basis of, for example, the following expression:

$$B_{OUT}=B_{IN}\times[\{(R_{IN}/F_{IN})-(1/\alpha)\}\times\beta+1],$$

$$G_{OUT}=G_{IN}, \text{ and}$$

$$R_{OUT}=R_{IN}\times[\{(R_{IN}/F_{IN})-(1/\alpha)\}\times\beta+1],$$

where $B_{OUT}$ is the signal strength of the B component of the corrected image, $G_{OUT}$ is the signal strength of the G component of the corrected image, $R_{OUT}$ is the signal strength of the R component of the corrected image, $B_{IN}$ is the signal strength of the B component of the white-light image, $G_{IN}$ is the signal strength of the G component of the white-light image, $R_{IN}$ is the signal strength of the R component of the white-light image, $F_{IN}$ is the signal strength of the fluorescence image, α is a coefficient that equals $R_{IN}/F_{IN}$ at a normal site, and β is color gain (coefficient set in advance).

By correcting the RGB components of the white-light image in this way, the B and R components of the corrected image can be decreased when the signal strength of the fluorescence image is increased. In addition, by including multiplication by the color gain, the color change in the affected site A1 can be increased. Accordingly, it is possible to display only the affected site A1 in green in the combined image, as well as to display the normal sites therein in the original color.

Fifth Modification

As a fifth modification of this embodiment, the image computing unit 25 may add results of dividing the fluorescence image generated by the fluorescence-image generating unit 21 by at least one signal among the R, G, and B components of the white-light image to the signals of the R, G, and B components of the white-light image.

Specifically, the image computing unit 25 corrects the color signals of the R, G, and B components of the white-light image on the basis of, for example, the following expressions:

$$B_{OUT}=B_{IN}+[\{(F_{IN}/R_{IN})-\alpha\}\times\beta],$$

$$G_{OUT}=G_{IN}, \text{ and}$$

$$R_{OUT}=R_{IN}+[\{(F_{IN}/R_{IN})-\alpha\}\times\beta],$$

where $B_{OUT}$ is the signal strength of the B component of the corrected image, $G_{OUT}$ is the signal strength of the G component of the corrected image, $R_{OUT}$ is the signal strength of the R component of the corrected image, $B_{IN}$ is the signal strength of the B component of the white-light image, $G_{IN}$ is the signal strength of the G component of the white-light image, $R_{IN}$ is the signal strength of the R component of the white-light image, $F_{IN}$ is the signal strength of the fluorescence image, α is a coefficient that equals $F_{IN}/R_{IN}$ at a normal site, and p is color gain (coefficient set in advance).

By correcting the RGB components of the white-light image in this way, because the B and R components are increased when the signal strength of the fluorescence image is increased, the affected site A1 appears in a color closer to magenta (purplish red). In addition, by including multiplication by the color gain, the color change in the affected site A1 can be increased. Accordingly, it is possible to display the affected site A1 in magenta (purplish red) in the combined image, as well as to display the normal sites therein in the original color.

Sixth Modification

As a sixth modification of this embodiment, the image computing unit 25 may subtract results of dividing the fluorescence image generated by the fluorescence-image generating unit 21 by at least one signal among the R, G, and B components of the white-light image from the signals of the R, G, and B components of the white-light image.

Specifically, the image computing unit 25 corrects the color signals of the R, G, and B components of the white-light image on the basis of, for example, the following expressions:

$$B_{OUT}=B_{IN}-[\{(F_{IN}/R_{IN})-\alpha\}\times\beta],$$

$$G_{OUT}=G_{IN}, \text{ and}$$

$$R_{OUT}=R_{IN}-[\{(F_{IN}/R_{IN})-\alpha\}\times\beta],$$

where $B_{OUT}$ is the signal strength of the B component of the corrected image, $G_{OUT}$ is the signal strength of the G component of the corrected image, $R_{OUT}$ is the signal strength of the R component of the corrected image, $B_{IN}$ is the signal strength of the B component of the white-light image, $G_{IN}$ is the signal strength of the G component of the white-light image, $R_{IN}$ is the R component of the white-light image, $F_{IN}$ is the signal strength of the fluorescence image, $\alpha$ is a coefficient that equals $F_{IN}/R_{IN}$ at a normal site, and $\beta$ is color gain (coefficient set in advance).

By correcting the RGB components of the white-light image in this way, the B and R components of the corrected image can be decreased when the signal strength of the fluorescence image is increased. In addition, by including multiplication by the color gain, the color change in the affected site A1 can be increased. Accordingly, it is possible to display only the affected site A1 in green in the combined image, as well as to display the normal sites therein in the original color.

Seventh Modification

As a seventh modification of this embodiment, the image computing unit 25 may add results of subtracting at least one signal of the R, G, and B components of the white-light image from the fluorescence image generated by the fluorescence-image generating unit 21 to the signals of the R, G, and B components of the white-light image.

Specifically, the image computing unit 25 corrects the color signals of the R, G, and B components of the white-light image on the basis of, for example, the following expressions:

$$B_{OUT}=B_{IN}+(F_{IN}-R_{IN}\times\alpha)\times\beta,$$

$$G_{OUT}=G_{IN}, \text{ and}$$

$$R_{OUT}=R_{IN}+(F_{IN}-R_{IN}\times\alpha)\times\beta,$$

where $B_{OUT}$ is the signal strength of the B component of the corrected image, $G_{OUT}$ is the signal strength of the G component of the corrected image, $R_{OUT}$ is the signal strength of the R component of the corrected image, $B_{IN}$ is the signal strength of the B component of the white-light image, $G_{IN}$ is the signal strength of the G component of the white-light image, $R_{IN}$ is the signal strength of the R component of the white-light image, $F_{IN}$ is the signal strength of the fluorescence image, $\alpha$ is a coefficient that equals $F_{IN}/R_{IN}$ at a normal site, and $\beta$ is color gain (coefficient set in advance).

By correcting the RGB components of the white-light image in this way, because the B and R components are increased when the signal strength of the fluorescence image is increased, the affected site A1 appears in a color closer to magenta (purplish red). In addition, by including multiplication by the color gain, the color change in the affected site A1 can be increased. Accordingly, it is possible to display the affected site A1 in magenta (purplish red) in the combined image, as well as to display the normal sites therein in the original color.

Eighth Modification

As an eighth modification of this embodiment, the image computing unit 25 may subtract results of subtracting at least one signal of the R, G, and B components of the white-light image from the fluorescence image generated by the fluorescence-image generating unit 21 from the signals of the R, G, and B components of the white-light image.

Specifically, the image computing unit 25 corrects the color signals of the R, G, and B components of the white-light image on the basis of, for example, the following expressions:

$$B_{OUT}=B_{IN}+(F_{IN}-R_{IN}\times\alpha)\times\beta,$$

$$G_{OUT}=G_{IN}, \text{ and}$$

$$R_{OUT}=R_{IN}+(F_{IN}-R_{IN}\times\alpha)\times\beta,$$

where $B_{OUT}$ is the signal strength of the B component of the corrected image, $G_{OUT}$ is the signal strength of the G component of the corrected image, $R_{OUT}$ is the signal strength of the R component of the corrected image, $B_{IN}$ is the signal strength of the B component of the white-light image, $G_{IN}$ is the signal strength of the G component of the white-light image, $R_{IN}$ is the signal strength of the R component of the white-light image, $F_{IN}$ is the signal strength of the fluorescence image, $\alpha$ is a coefficient that equals $F_{IN}/R_{IN}$ at a normal site, and $\beta$ is color gain (coefficient set in advance).

By correcting the RGB components of the white-light image in this way, the B and R components of the corrected image can be decreased when the signal strength of the fluorescence image is increased. In addition, by including multiplication by the color gain, the color change in the affected site A1 can be increased. Accordingly, it is possible to display only the affected site A1 in green in the combined image, as well as to display the normal sites therein in the original color.

In the third to eighth modifications, the color gain $\beta$ is a coefficient set in advance assuming that the ratio of the fluorescence intensities between the normal sites and affected site A1 in the subject A is known in advance. The color gain $\beta$ is preferably a value that intensifies the color change in the affected site A1. In the third, fifth, and seventh modifications, the color gain $\beta$ is determined such that the signal strength does not become saturated, and, in the sixth and eight modifications, it is determined such that the signal strength is not a negative value (or is set to zero when the signal strength is a negative value).

Ninth Modification

As a ninth modification of this embodiment, the image computing unit 25 may include an HSV converting unit (not shown) that performs the HSV conversion on the signals of the R, G, and B components of the white-light image, and the image computing unit 25 may correct the H component signal converted by the HSV converting unit.

Specifically, the HSV converting unit converts the signals of the R, G, and B components of the white-light image stored in the memory 24 to V (brightness), S (saturation), and H (hue) components, respectively.

$$V=\text{Max}(R,G,B)$$

$$S=1-\text{Min}(R,G,B)/\text{Max}(R,G,B)$$

$$H=60\times((G-B)/(R-\text{Min}(R,G,B)))$$

The image computing unit 25 corrects the H component (hue) of the white-light image on the basis of, for example, the following expressions:

$$H = H \times (F_{IN}/R_{IN}) \times \alpha$$

where H is the signal strength of the H component of the white-light image, S is the signal strength of the S component of the white-light image, V is the signal strength of the V component of the white-light image, B is the signal strength of the B component of the white-light image, G is the signal strength of the G component of the white-light image, R is the signal strength of the R component of the white-light image, $R_{IN}$ is the signal strength of the R component of the white-light image, $F_{IN}$ is the signal strength of the fluorescence image, and $\alpha$ is a coefficient that equals $R_{IN}/F_{IN}$ at a normal site.

In this way, the color of the affected site can be changed to a color that does not exist in a biological subject, such as green, blue, and so forth, which makes it possible to improve the observation precision of the affected site A1.

Note that, in this modification, a correction method according to the second to eight modifications described above may be applied to the correction of the H component (hue) of the white-light image.

In addition, in this modification, not only the H component (hue) of the white-light image but also the V component (brightness) and S component (saturation) may be corrected.

Tenth Modification

As a tenth modification of this embodiment, the signals of the R, G, and B components of the white-light image may be acquired through a frame sequential method.

Figure 6:
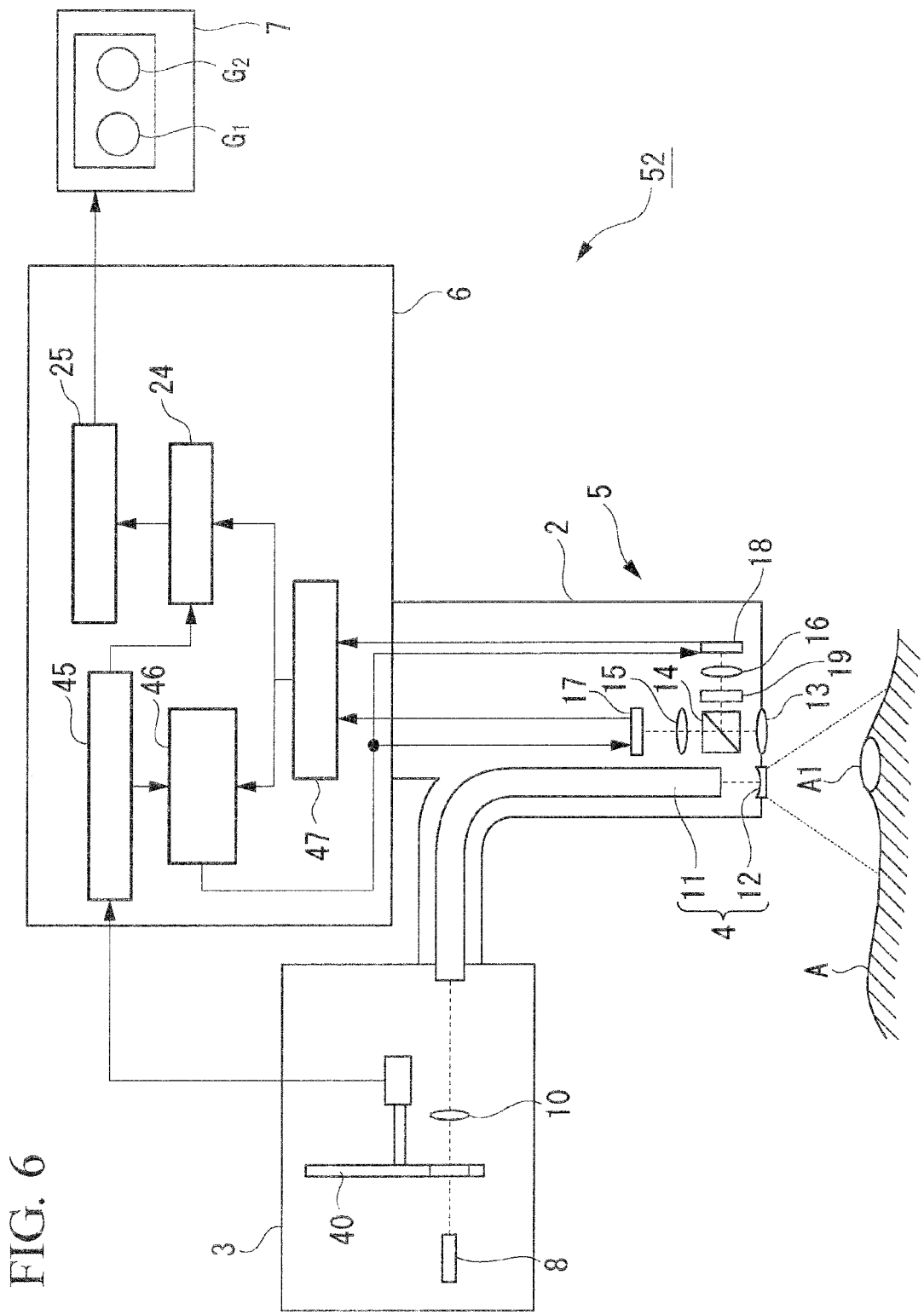
FIG. 6 is a schematic configuration diagram of a fluoroscopy device according to a tenth modification of the present invention.

In a fluoroscopy device 52 according to this modification, as illustrated in FIG. 6, a light source 3 includes a xenon lamp 8, a wavelength selecting unit 40 that selects and transmits a desired wavelength band in the illumination light emitted from the xenon lamp 8, and a coupling lens 10 that focuses the excitation light and the white light separated by the wavelength selecting unit 40.

Figure 7:
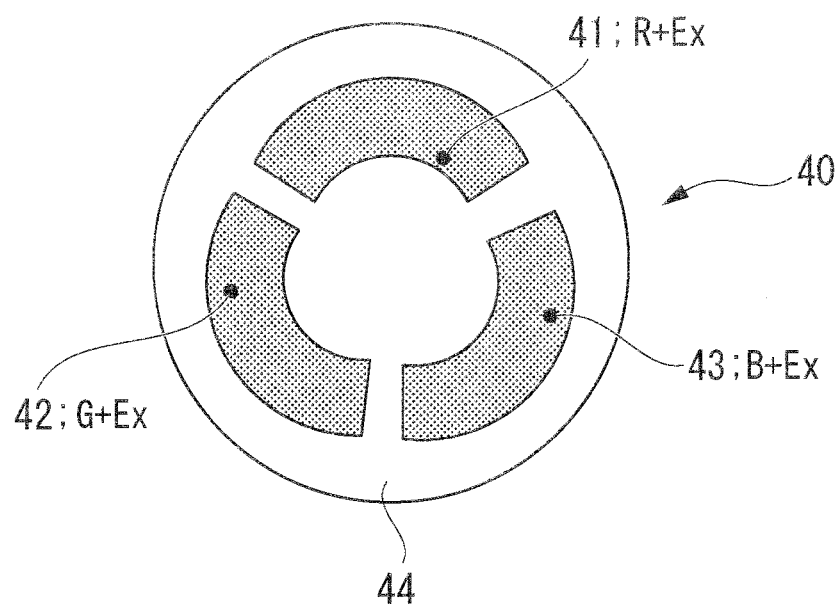
FIG. 7 is a diagram showing, in outline, the configuration of a wavelength selecting unit in FIG. 6.

As illustrated in FIG. 7, the wavelength selecting unit 40 includes a turret 44 that is rotated by, for example, a motor or the like and a plurality of filters 41, 42, and 43 that transmit light in different wavelength bands.

Figure 8:
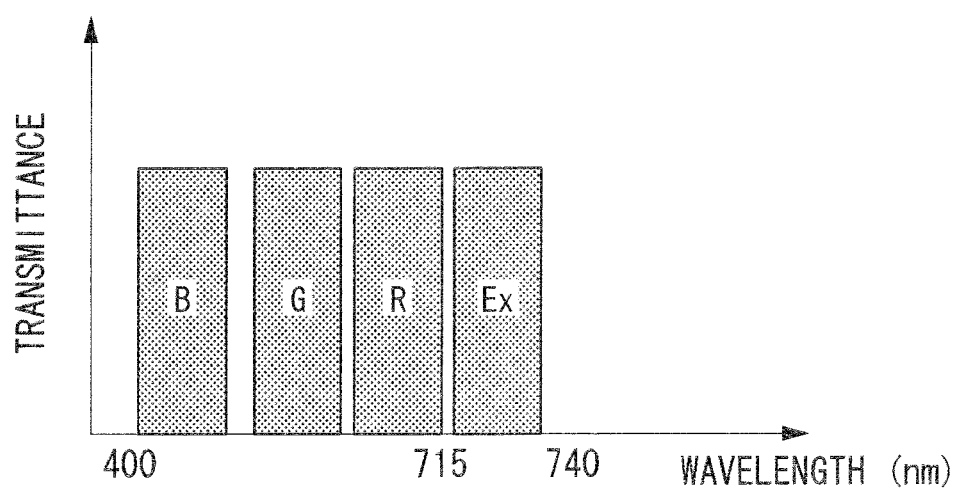
FIG. 8 is a graph showing the transmission characteristics of individual filters in FIG. 7.

As illustrated in FIG. 8, the filter 41 has a characteristic of transmitting only the R component of the white-light image and excitation light EX (for example, light in the wavelength band of 715 to 740 nm). Similarly, the filter 42 has a characteristic of transmitting only the G component of the white-light image and excitation light EX, and the filter 43 has a characteristic of transmitting only the B component of the white-light image and excitation light EX.

As illustrated in FIG. 6, the image processing device 6 includes, as functions thereof, an image generating unit (return-light-image generating unit, fluorescence-image generating unit) 47 that generates a white-light image and a fluorescence image, an exposure-time automatic adjusting unit 46 that adjusts the exposure time of the white-light color CCD 17 and the fluorescence monochrome CCD 18, a memory (color converting unit) 24 that stores the color signals of the R, G, and B components of the white-light image, an image computing unit (color-signal correcting unit, corrected-image generating unit, image combining unit) 25 that corrects the color signals of the R, G, and B components, and a timing control unit 45 that controls the timing for storing in the memory 24 in synchronization with the rotation of the turret 44 of the wavelength selecting unit 40.

Note that although the image generating unit 47 in this modification has a function that combines the white-light-image generating unit 20 and the fluorescence-image generating unit 21 in FIG. 1, the white-light-image generating unit 20 and the fluorescence-image generating unit 21 may be provided separately as in FIG. 1.

In addition, although the exposure-time automatic adjustment unit 46 has a function that combines the automatic exposure-time adjusting unit 22 and the automatic exposure-time adjusting unit 23 in FIG. 1, the automatic exposure-time adjusting unit 22 and the automatic exposure-time adjusting unit 23 may be provided separately as in FIG. 1.

Figure 9:
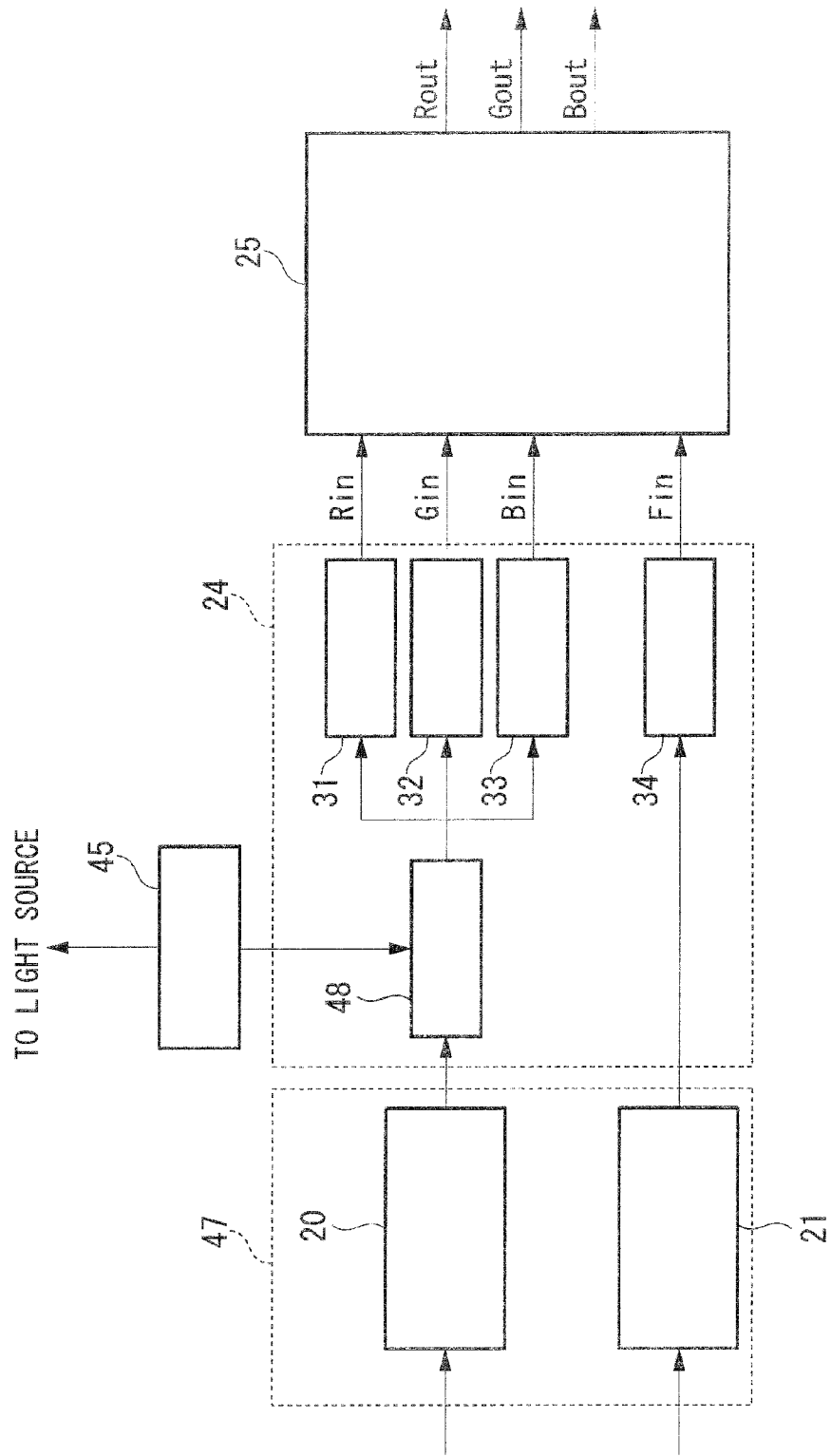
FIG. 9 is a functional block diagram of the image processing device in FIG. 6.

As illustrated in FIG. 9, the memory 24 includes an R memory 31, a G memory 32, and a B memory 33 that respectively store the color signals of the R, G, and B components of the white-light image, an F memory 34 that stores the fluorescence-image signal, and a selector 48 that selects to which memory the white-light image should be output.

The selector 48 is controlled by the timing control unit 45 and selects to which of the R memory 31, the G memory 32, and the B memory 33 the white-light image should be output in synchronization with the rotation of the turret 44 of the wavelength selecting unit 40.

Specifically, the acquired white-light image is stored in the R memory 31 at a timing at which the filter 41, which transmits the R component of the white-light image and the excitation light EX, is positioned on the emitted-light axis of the xenon lamp 8. Similarly, the white-light image acquired at a timing when the filter 42 is positioned on the emitted-light axis of the xenon lamp 8 is stored in the G memory 32, and the white-light image acquired at a timing when the filter 43 is positioned on the emitted-light axis of the xenon lamp 8 is stored in the B memory 33.

By doing so, the white-light image acquired by the image generating unit 47 can be divided into color signals of the R, G, and B components, without requiring color conversion, and the color signals of the R, G, and B components can be corrected by the image computing unit 25. Accordingly, similar to the above-described modifications, the combined image in which the normal sites are corrected so as to appear with equivalent colors to the original can be displayed on the monitor 7.

Eleventh Modification

Figure 10:
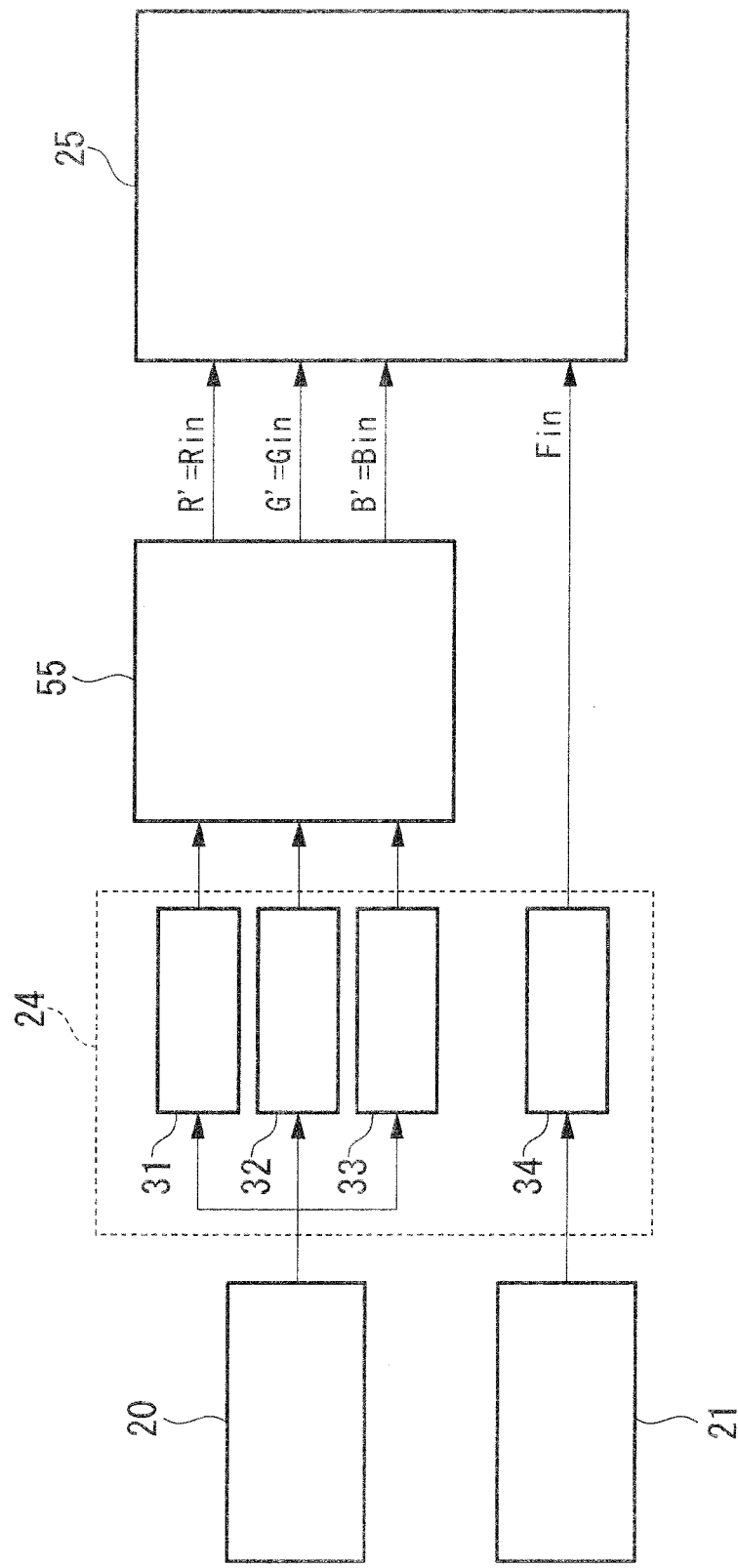
FIG. 10 is a functional block diagram of an image processing device of a fluoroscopy device according to an eleventh modification of the present invention.

As an eleventh modification of this embodiment, as illustrated in FIG. 10, a color matrix circuit 55 that performs color correction on the signals of the R, G, and B components may be provided between the memory 24 and the image computing unit 25.

Specifically, the color matrix circuit 55 performs color correction on the individual signals by performing computation represented by the following expression on the signals of the R, G, and B components.

$$\begin{pmatrix} R' \\ G' \\ B' \end{pmatrix} = \begin{pmatrix} M_{11} & M_{12} & M_{13} \\ M_{21} & M_{22} & M_{23} \\ M_{31} & M_{32} & M_{33} \end{pmatrix} \begin{pmatrix} R \\ G \\ B \end{pmatrix} \quad \{\text{Expression 1}\}$$

where R', G', and B' respectively represent the signal strengths of the color-corrected (i.e., after color correction) R, G, and B components, $M_{11}$ to $M_{33}$ are coefficients set in advance, and R, G, and B respectively represent the signal strengths of the color (i.e., before color correction)$_R$, G, and B components.

By doing so, the color-corrected color signals of the R, G, and B components can be further corrected by the image computing unit 25. Accordingly, the combined image in which the normal sites are corrected so as to appear with equivalent colors to the original can be displayed.

Twelfth Modification

Figure 11:
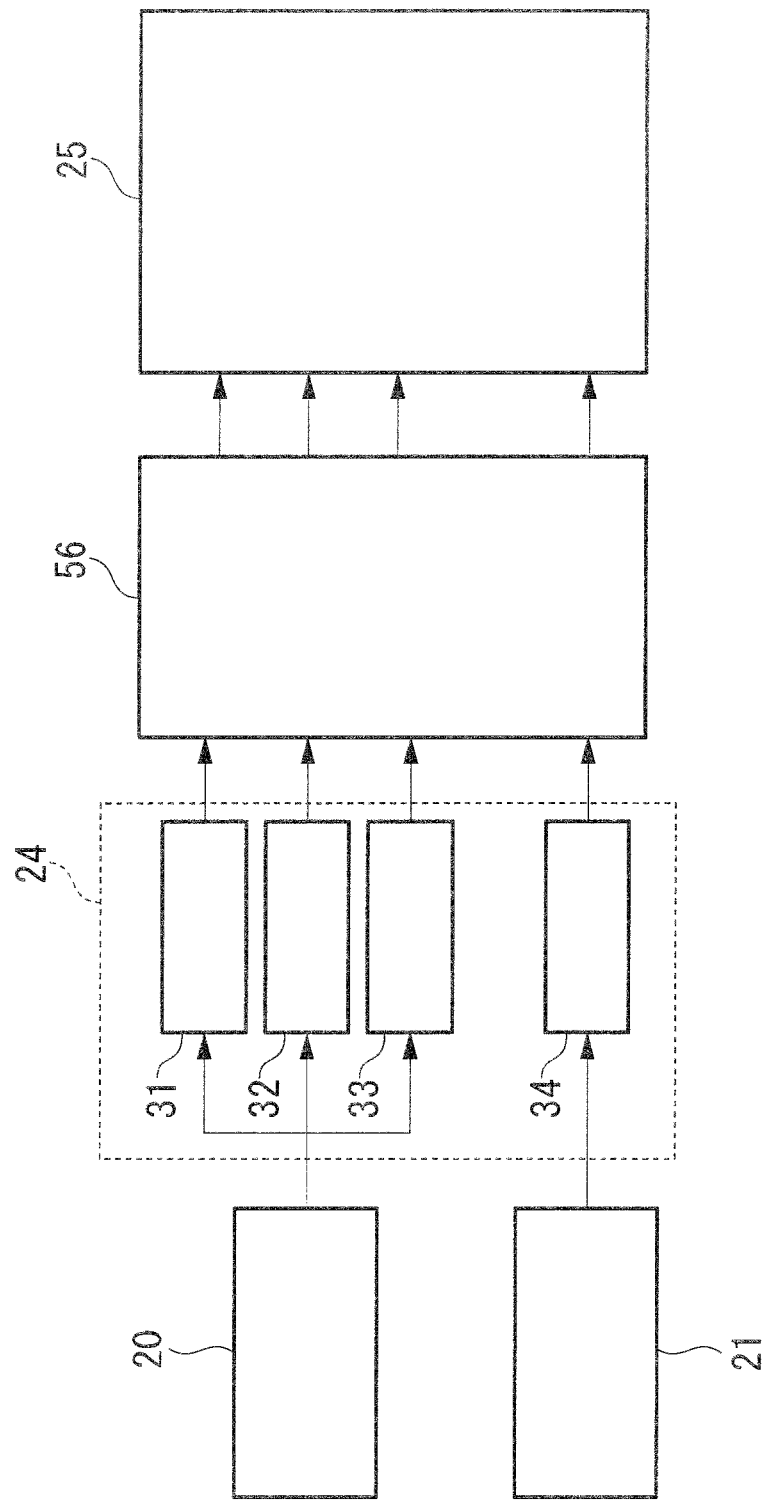
FIG. 11 is a functional block diagram of an image processing device of a fluoroscopy device according to a twelfth modification of the present invention.

As a twelfth modification of this embodiment, as illustrated in FIG. 11, a pre-processing unit 56 that generates a corrected fluorescence image by normalizing the fluorescence image generated by the fluorescence-image generating unit 21 based on the white-light image generated by the white-light-image generating unit 20 may be provided between the memory 24 and the image computing unit 25.

The pre-processing unit 56 generates a corrected fluorescence image in which luminance values of individual pixels have been normalized by dividing the luminance values of the individual pixels in the fluorescence image generated by the fluorescence-image generating unit 21 by the luminance values of the individual pixels of the white-light image generated by the white-light-image generating unit 20 corresponding to the individual pixels in the fluorescence image.

By doing so, the corrected fluorescence image in which the luminance values of the individual pixels have been normalized and the corrected image in which the R, G, and B components of the white-light image have been corrected can be combined and displayed on the monitor 7. Accordingly, the normal sites corrected so as to appear with colors of greater equivalence to the original can be displayed, and the condition of the subject A can also be determined by eliminating the effect of the observation distance and observation angle on the fluorescence intensity, thus making possible to improve the observation precision of the affected site A1.

Although an embodiment of the present invention has been described above in detail with reference to the drawings, the specific configurations are not limited to this embodiment, and design alterations or the like that do not depart from the scope of the invention are encompassed by the present invention.

For example, although this embodiment describes a case in which the image processing device and the fluoroscopy device according to the present invention are applied to an endoscope apparatus, the devices may be applied to a microscope apparatus or the like.

The present invention is not limited to applications of the above-described embodiment and modifications and may be applied to an embodiment that appropriately combines the modifications.

Additionally, although, in this embodiment, the signal of the R component of the white-light image and the fluorescence-image signal are used in the correction of the signal strengths of the signals of the R, G, and B components of the white-light image, the G or B component of the white-light image and the fluorescence-image signal may be used. Also, the fluorescence-image signal and any two or more signals among the R, G, and B components of the white-light image may be used.

In addition, although this embodiment describes a case in which the signal strengths of the R and B components of the white-light image are corrected, the signal strength of any of the R, G, and B components of the white-light image may be corrected. Also, the signal strengths of any two or more components among the R, G, and B components of the white-light image may be corrected.

REFERENCE SIGNS LIST

A subject
A1 affected site
1, 51, 52 fluoroscopy device
2 insertion part
3 light source (light source unit)
4 illumination unit
5 image acquisition unit
6 image processing device
7 monitor (image display unit)
20 white-light-image generating unit (return-light-image acquiring unit)
21 fluorescence-image generating unit (fluorescence-image acquiring unit)
22 automatic exposure-time adjusting unit
23 automatic exposure-time adjusting unit
24 memory (color converting unit)
25 image computing unit (color-signal correcting unit, corrected-image generating unit, image combining unit)
28 input unit
29 parameter setting unit
31 R memory
32 G memory
33 B memory
34 F memory
40 wavelength selecting unit
45 timing control unit
46 exposure-time automatic adjusting unit
47 image generating unit
55 color matrix circuit
56 pre-processing unit The present invention is advantageous in that an affected site can be easily identified and a change in the color of a normal site can be suppressed.

The invention claimed is:

1. An image processing device comprising hardware, the image processing device being configured to implement:

a fluorescence-image generating unit configured to image fluorescence generated at a subject irradiated with excitation light and generate a fluorescence image;

a return-light-image generating unit configured to image return light returned from the subject irradiated with illumination light and generate a return-light image;

a color converting unit configured to convert the return-light image generated by the return-light-image generating unit to a plurality of return-light image color signals constituting a color space;

a color-signal correcting unit configured to correct the plurality of return-light image color signals converted by the color converting unit using both of: (a) at least one color signal among the plurality of return-light image color signals; and (b) the fluorescence image generated by the fluorescence-image generating unit;

a corrected-image generating unit configured to generate a corrected return-light image from the plurality of return-light image color signals corrected by the color-signal correcting unit; and an image combining unit configured to combine the fluorescence image generated by the fluorescence-image generating unit and the corrected return-light image generated by the corrected-image generating unit;

wherein the plurality of return-light image color signals comprise signals of R, G, and B components of the return-light image; and wherein the color-signal correcting unit multiplies results of dividing the fluorescence image generated by the fluorescence-image generating unit by at least one signal among the R, G, and B components of the return-light image with the signals of the R, G, and B components of the return-light image.

2. The image processing device according to claim 1, wherein the color-signal correcting unit corrects the R, G, and B components of the return-light image based on the following expressions:

$$B_{OUT}=B_{IN}\times(F_{IN}/R_{IN})\times\alpha,$$

$$G_{OUT}=G_{IN}, \text{ and}$$

$$R_{OUT}=R_{IN}\times(F_{IN}/R_{IN})\times\alpha,$$

where $B_{OUT}$ is the signal strength of the B component of the corrected return-light image, $G_{OUT}$ is the signal strength of the G component of the corrected return-light image, $R_{OUT}$ is the signal strength of the R component of the corrected return-light image, $B_{IN}$ is the signal strength of the B component of the return-light image, $G_{IN}$ is the signal strength of the G component of the return-light image, $R_{IN}$ is the signal strength of the R component of the return-light image, $F_{IN}$ is the signal strength of the fluorescence image, and a is a coefficient that equals $R_{IN}/F_{IN}$ at a normal site.

3. An image processing device comprising hardware, the image processing device being configured to implement:
a fluorescence-image generating unit configured to image fluorescence generated at a subject irradiated with excitation light and generate a fluorescence image;
a return-light-image generating unit configured to image return light returned from the subject irradiated with illumination light and generate a return-light image;
a color converting unit configured to convert the return-light image generated by the return-light-image generating unit to a plurality of return-light image color signals constituting a color space;
a color-signal correcting unit configured to correct the plurality of return-light image color signals converted by the color converting unit using both of: (a) at least one color signal among the plurality of return-light image color signals; and (b) the fluorescence image generated by the fluorescence-image generating unit;
a corrected-image generating unit configured to generate a corrected return-light image from the plurality of return-light image color signals corrected by the color-signal correcting unit; and
an image combining unit configured to combine the fluorescence image generated by the fluorescence-image generating unit and the corrected return-light image generated by the corrected-image generating unit;
wherein the plurality of return-light image color signals comprise signals of R, G, and B components of the return-light image; and
wherein the color-signal correcting unit multiplies results of dividing at least one signal among the R, G, and B components of the return-light image by the fluorescence image generated by the fluorescence-image generating unit with the signals of the R, G, and B components of the return-light image.

4. The image processing device according to claim 3, wherein the color-signal correcting unit corrects the R, G, and B components of the return-light image based on the following expressions:

$$B_{OUT}=B_{IN}\times(F_{IN}/R_{IN})\times\alpha,$$

$$G_{OUT}=G_{IN}, \text{ and}$$

$$R_{OUT}=R_{IN}\times(F_{IN}/R_{IN})\times\alpha,$$

where $B_{OUT}$ is the signal strength of the B component of the corrected return-light image, $G_{OUT}$ is the signal strength of the G component of the corrected return-light image, $R_{OUT}$ is the signal strength of the R component of the corrected return-light image, $B_{IN}$ is the signal strength of the B component of the return-light image, $G_{IN}$ is the signal strength of the G component of the return-light image, $R_{IN}$ is the signal strength of the R component of the return-light image, $F_{IN}$ is the signal strength of the fluorescence image, and a is a coefficient that equals $R_{IN}/F_{IN}$ at a normal site.

5. An image processing device comprising hardware, the image processing device being configured to implement:
a fluorescence-image generating unit configured to image fluorescence generated at a subject irradiated with excitation light and generate a fluorescence image;
a return-light-image generating unit configured to image return light returned from the subject irradiated with illumination light and generate a return-light image;
a color converting unit configured to convert the return-light image generated by the return-light-image generating unit to a plurality of return-light image color signals constituting a color space;
a color-signal correcting unit configured to correct the plurality of return-light image color signals converted by the color converting unit using both of: (a) at least one color signal among the plurality of return-light image color signals; and (b) the fluorescence image generated by the fluorescence-image generating unit;
a corrected-image generating unit configured to generate a corrected return-light image from the plurality of return-light image color signals corrected by the color-signal correcting unit; and
an image combining unit configured to combine the fluorescence image generated by the fluorescence-image generating unit and the corrected return-light image generated by the corrected-image generating unit;
wherein the plurality of return-light image color signals comprise signals of R, G, and B components of the return-light image; and
wherein the color-signal correcting unit corrects the R, G, and B components of the return-light image based on the following expressions:

$$B_{OUT}=B_{IN}\times[\{(F_{IN}/R_{IN})-\alpha\}\times\beta+1],$$

$$G_{OUT}=G_{IN}, \text{ and}$$

$$R_{OUT}=R_{IN}\times[\{(F_{IN}/R_{IN})-\alpha\}\times\beta+1],$$

where $B_{OUT}$ is the signal strength of the B component of the corrected return-light image, $G_{OUT}$ is the signal strength of the G component of the corrected return-light image, $R_{OUT}$ is the signal strength of the R component of the corrected return-light image, $B_{IN}$ is the signal strength of the B component of the return-light image, $G_{IN}$ is the signal strength of the G component of the return-light image, $R_{IN}$ is the signal strength of the R component of the return-light image, $F_{IN}$ is the signal strength of the fluorescence image, $\alpha$ is a coefficient that equals $F_{IN}/R_{IN}$ at a normal site, and $\beta$ is a color gain coefficient set in advance.

6. An image processing device comprising hardware, the image processing device being configured to implement:
a fluorescence-image generating unit configured to image fluorescence generated at a subject irradiated with excitation light and generate a fluorescence image;
a return-light-image generating unit configured to image return light returned from the subject irradiated with illumination light and generate a return-light image;
a color converting unit configured to convert the return-light image generated by the return-light-image generating unit to a plurality of return-light image color signals constituting a color space;

a color-signal correcting unit configured to correct the plurality of return-light image color signals converted by the color converting unit using both of: (a) at least one color signal among the plurality of return-light image color signals; and (b) the fluorescence image generated by the fluorescence-image generating unit;

a corrected-image generating unit configured to generate a corrected return-light image from the plurality of return-light image color signals corrected by the color-signal correcting unit; and an image combining unit configured to combine the fluorescence image generated by the fluorescence-image generating unit and the corrected return-light image generated by the corrected-image generating unit;

wherein the plurality of return-light image color signals comprise signals of R, G, and B components of the return-light image; and wherein the color-signal correcting unit corrects the R, G, and B components of the return-light image based on the following expressions:

$$B_{OUT}=B_{IN}\times[\{(R_{IN}/F_{IN})-(1/\alpha)\}\times\beta+1],$$

$$G_{OUT}=G_{IN}, \text{ and}$$

$$R_{OUT}=R_{IN}\times[\{(R_{IN}/F_{IN})-(1/\alpha)\}\times\beta+1],$$

where $B_{OUT}$ is the signal strength of the B component of the corrected return-light image, $G_{OUT}$ is the signal strength of the G component of the corrected return-light image, $R_{OUT}$ is the signal strength of the R component of the corrected return-light image, $B_{IN}$ is the signal strength of the B component of the return-light image, $G_{IN}$ is the signal strength of the G component of the return-light image, $R_{IN}$ is the signal strength of the R component of the return-light image, $F_{IN}$ is the signal strength of the fluorescence image, $\alpha$ is a coefficient that equals $R_{IN}/F_{IN}$ at a normal site, and $\beta$ is a color gain coefficient set in advance.

7. An image processing device comprising hardware, the image processing device being configured to implement:

a fluorescence-image generating unit configured to image fluorescence generated at a subject irradiated with excitation light and generate a fluorescence image;

a return-light-image generating unit configured to image return light returned from the subject irradiated with illumination light and generate a return-light image;

a color converting unit configured to convert the return-light image generated by the return-light-image generating unit to a plurality of return-light image color signals constituting a color space;

a color-signal correcting unit configured to correct the plurality of return-light image color signals converted by the color converting unit using both of: (a) at least one color signal among the plurality of return-light image color signals; and (b) the fluorescence image generated by the fluorescence-image generating unit;

a corrected-image generating unit configured to generate a corrected return-light image from the plurality of return-light image color signals corrected by the color-signal correcting unit; and an image combining unit configured to combine the fluorescence image generated by the fluorescence-image generating unit and the corrected return-light image generated by the corrected-image generating unit;

wherein the plurality of return-light image color signals comprise signals of R, G, and B components of the return-light image; and wherein the color-signal correcting unit adds results of dividing the fluorescence image generated by the fluorescence-image generating unit by at least one signal among the R, G, and B components of the return-light image to the signals of the R, G, and B components of the return-light image.

8. The image processing device according to claim 7, wherein the color-signal correcting unit corrects the R, G, and B components of the return-light image based on the following expressions:

$$B_{OUT}=B_{IN}+[\{(F_{IN}/R_{IN})-\alpha\}\times\beta],$$

$$G_{OUT}=G_{IN}, \text{ and}$$

$$R_{OUT}=R_{IN}+[\{(F_{IN}/R_{IN})-\alpha\}\times\beta],$$

where $B_{OUT}$ is the signal strength of the B component of the corrected return-light image, $G_{OUT}$ is the signal strength of the G component of the corrected return-light image, $R_{OUT}$ is the signal strength of the R component of the corrected return-light image, $B_{IN}$ is the signal strength of the B component of the return-light image, $G_{IN}$ is the signal strength of the G component of the return-light image, $R_{IN}$ is the signal strength of the R component of the return-light image, $F_{IN}$ is the signal strength of the fluorescence image, $\alpha$ is a coefficient that equals $F_{IN}/R_{IN}$ at a normal site, and $\beta$ is a color gain coefficient set in advance.

9. An image processing device comprising hardware, the image processing device being configured to implement:

a fluorescence-image generating unit configured to image fluorescence generated at a subject irradiated with excitation light and generate a fluorescence image;

a return-light-image generating unit configured to image return light returned from the subject irradiated with illumination light and generate a return-light image;

a color converting unit configured to convert the return-light image generated by the return-light-image generating unit to a plurality of return-light image color signals constituting a color space;

a color-signal correcting unit configured to correct the plurality of return-light image color signals converted by the color converting unit using both of: (a) at least one color signal among the plurality of return-light image color signals; and (b) the fluorescence image generated by the fluorescence-image generating unit;

a corrected-image generating unit configured to generate a corrected return-light image from the plurality of return-light image color signals corrected by the color-signal correcting unit; and an image combining unit configured to combine the fluorescence image generated by the fluorescence-image generating unit and the corrected return-light image generated by the corrected-image generating unit;

wherein the plurality of return-light image color signals comprise signals of R, G, and B components of the return-light image; and wherein the color-signal correcting unit subtracts results of dividing the fluorescence image generated by the fluorescence-image generating unit by at least one signal among the R, G, and B components of the return-light image from the signals of the R, G, and B components of the return-light image.

10. The image processing device according to claim 9, wherein the color-signal correcting unit corrects the R, G, and B components of the return-light image based on the following expressions:

$$B_{OUT}=B_{IN}-[\{(F_{IN}/R_{IN})-\alpha\}\times\beta],$$

$$G_{OUT}=G_{IN}, \text{ and}$$

$$R_{OUT}=R_{IN}-[\{(F_{IN}/R_{IN})-\alpha\}\times\beta],$$

where $B_{OUT}$ is the signal strength of the B component of the corrected return-light image, $G_{OUT}$ is the signal strength of the G component of the corrected return-light image, $R_{OUT}$ is the signal strength of the R component of the corrected return-light image, $B_{IN}$ is the signal strength of the B component of the return-light image, $G_{IN}$ is the signal strength of the G component of the return-light image, $R_{IN}$ is the signal strength of the R component of the return-light image, $F_{IN}$ is the signal strength of the fluorescence image, $\alpha$ is a coefficient that equals $F_{IN}/R_{IN}$ at a normal site, and $\beta$ is a color gain coefficient set in advance.

11. An image processing device comprising hardware, the image processing device being configured to implement:
a fluorescence-image generating unit configured to image fluorescence generated at a subject irradiated with excitation light and generate a fluorescence image;
a return-light-image generating unit configured to image return light returned from the subject irradiated with illumination light and generate a return-light image;
a color converting unit configured to convert the return-light image generated by the return-light-image generating unit to a plurality of return-light image color signals constituting a color space;
a color-signal correcting unit configured to correct the plurality of return-light image color signals converted by the color converting unit using both of: (a) at least one color signal among the plurality of return-light image color signals; and (b) the fluorescence image generated by the fluorescence-image generating unit;
a corrected-image generating unit configured to generate a corrected return-light image from the plurality of return-light image color signals corrected by the color-signal correcting unit; and
an image combining unit configured to combine the fluorescence image generated by the fluorescence-image generating unit and the corrected return-light image generated by the corrected-image generating unit;
wherein the plurality of return-light image color signals comprise signals of R, G, and B components of the return-light image; and
wherein the color-signal correcting unit adds results of subtracting the fluorescence image generated by the fluorescence-image generating unit from at least one signal among the R, G, and B components of the return-light image to the signals of the R, G, and B components of the return-light image.

12. The image processing device according to claim 11, wherein the color-signal correcting unit corrects the R, G, and B components of the return-light image based on the following expressions:

$$B_{OUT}=B_{IN}+(F_{IN}-R_{IN}\times\alpha)\times\beta,$$

$$G_{OUT}=G_{IN}, \text{ and}$$

$$R_{OUT}=R_{IN}+(F_{IN}-R_{IN}\times\alpha)\times\beta,$$

where $B_{OUT}$ is the signal strength of the B component of the corrected return-light image, $G_{OUT}$ is the signal strength of the G component of the corrected return-light image, $R_{OUT}$ is the signal strength of the R component of the corrected return-light image, $B_{IN}$ is the signal strength of the B component of the return-light image, $G_{IN}$ is the signal strength of the G component of the return-light image, $R_{IN}$ is the signal strength of the R component of the return-light image, $F_{IN}$ is the signal strength of the fluorescence image, $\alpha$ is a coefficient that equals $F_{IN}/R_{IN}$ at a normal site, and $\beta$ is a color gain coefficient set in advance.

13. An image processing device comprising hardware, the image processing device being configured to implement:
a fluorescence-image generating unit configured to image fluorescence generated at a subject irradiated with excitation light and generate a fluorescence image;
a return-light-image generating unit configured to image return light returned from the subject irradiated with illumination light and generate a return-light image;
a color converting unit configured to convert the return-light image generated by the return-light-image generating unit to a plurality of return-light image color signals constituting a color space;
a color-signal correcting unit configured to correct the plurality of return-light image color signals converted by the color converting unit using both of: (a) at least one color signal among the plurality of return-light image color signals; and (b) the fluorescence image generated by the fluorescence-image generating unit;
a corrected-image generating unit configured to generate a corrected return-light image from the plurality of return-light image color signals corrected by the color-signal correcting unit; and
an image combining unit configured to combine the fluorescence image generated by the fluorescence-image generating unit and the corrected return-light image generated by the corrected-image generating unit;
wherein the plurality of return-light image color signals comprise signals of R, G, and B components of the return-light image; and
wherein the color-signal correcting unit subtracts results of subtracting the fluorescence image generated by the fluorescence-image generating unit from at least one signal among the R, G, and B components of the return-light image from the signals of the R, G, and B components of the return-light image.

14. The image processing device according to claim 13, wherein the color-signal correcting unit corrects the R, G, and B components of the return-light image based on the following expressions:

$$B_{OUT}=B_{IN}-(F_{IN}-R_{IN}\times\alpha)\times\beta,$$

$$G_{OUT}=G_{IN}, \text{ and}$$

$$R_{OUT}=R_{IN}-(F_{IN}-R_{IN}\times\alpha)\times\beta,$$

where $B_{OUT}$ is the signal strength of the B component of the corrected return-light image, $G_{OUT}$ is the signal strength of the G component of the corrected return-light image, $R_{OUT}$ is the signal strength of the R component of the corrected return-light image, $B_{IN}$ is the signal strength of the B component of the return-light image, $G_{IN}$ is the signal strength of the G component of the return-light image, $R_{IN}$ is the signal strength of the R component of the return-light image, $F_{IN}$ is the signal strength of the fluorescence image, $\alpha$ is a coefficient that equals $F_{IN}/R_{IN}$ at a normal site, and $\beta$ is a color gain coefficient set in advance.

15. An image processing method, comprising:
- imaging fluorescence generated at a subject irradiated with excitation light and generating a fluorescence image;
- imaging return light returned from the subject irradiated with illumination light and generating a return-light image;
- converting the generated return-light image to a plurality of return-light image color signals constituting a color space, the plurality of return-light image color signals comprising signals of R, G, and B components of the return-light image;
- correcting the plurality of return-light image color signals using both of: (a) at least one color signal among the plurality of return-light image color signals; and (b) the generated fluorescence image;
- multiplying results of dividing the fluorescence image by at least one signal among the R, G, and B components of the return-light image with the signals of the R, G, and B components of the return-light image;
- generating a corrected return-light image from the plurality of corrected return-light image color signals; and
- combining the generated fluorescence image and the corrected return-light image.

* * * * *